United States Patent [19]

Labat

[11] Patent Number: 5,001,271
[45] Date of Patent: Mar. 19, 1991

[54] SYNTHESIS OF BENZYL MERCAPTAN

[75] Inventor: Yves Labat, Pau, France

[73] Assignee: Societe Nationale Elf Aquitaine (Production), Courbevoie, France

[21] Appl. No.: 335,365

[22] Filed: Apr. 10, 1989

[30] Foreign Application Priority Data

Apr. 14, 1988 [FR] France .................. 88 04963

[51] Int. Cl.$^5$ .......................... C07C 319/02
[52] U.S. Cl. ......................................... 568/67
[58] Field of Search ................. 568/68, 67, 70

[56] References Cited

U.S. PATENT DOCUMENTS 2,456,588 12/1948 Loverde.
4,082,790 4/1978 Speier .................... 568/61
4,740,623 4/1988 Heather ................. 568/68

FOREIGN PATENT DOCUMENTS 61-145158 7/1986 Japan .................... 568/68

OTHER PUBLICATIONS

Derwent and Japio abstracts of Japanese patent 61-145158 published Jul. 1986.
J. E. Bittell et al, J. Org. Chem. 43, 1687 (1978).
H. Zinner, Chem. Ber. 86, 825 (1953).
C. Marcker, Liebigs Ann. Chem. 136, 76 (1865).

*Primary Examiner*—Mary E. Ceperley
*Attorney, Agent, or Firm*—Morgan & Finnegan

[57] ABSTRACT

This invention relates to the preparation of benzyl mercaptan by reacting benzyl chloride and ammonium sulfhydrate.

In the process according to the invention, the reaction is carried out under autogenous pressure in a closed reactor in two steps. The first comprises adding the benzyl chloride to an aqueous solution of ammonium sulfhydrate at a temperature below 80° C. The second comprises heating the reaction mixture to a temperature in the range 80° to 100° C.

5 Claims, No Drawings

SYNTHESIS OF BENZYL MERCAPTAN

FIELD OF THE INVENTION

The present invention relates to the field of mercaptans. More particularly, its subject is the preparation of benzyl mercaptan also known by the name thiobenzyl alcohol.

BACKGROUND OF THE INVENTION

Benzyl mercaptan is particularly useful as a raw material for the synthesis of herbicides in the thiocarbamate family. An excellent purity of benzyl mercaptan is required for this use.

The synthesis of benzyl mercaptan by the action of hydrogen sulphide on benzyl alcohol in the presence of a catalyst is not economically viable due to the high price of benzyl alcohol and its undesirable characteristics during catalysis (deactivation of catalysts and rapid loss of selectivity).

An economically more attractive synthetic route is the nucleophilic substitution of the chlorine atom in benzyl chloride by an alkaline sulfhydrate, ammonium sulfhydrate or an amine sulfhydrate. This reaction, generally carried out in an alcoholic medium, has long been known:

C. Marcker, Liebigs Ann. Chem. 136, 76 (1865)
U.S. Pat. No. 2,456,588 (1948)
H. Zinner, Chem. Ber. 86, 825 (1953)
J. E. Bittell et al, J. Org. Chem. 43, 1687 (1978)
U.S. Pat. No. 4,082,790 (1978)

but the yields obtained are modest and conversion is incomplete. These references are hereby incorporated by reference. According to U.S. Pat. No. 4,082,790, the use of butylamine sulfhydrate in a medium of isopropanol gives a mixture containing 10% of unconverted benzyl chloride, 82% of benzyl mercaptan and 6% of benzyl sulphide. The use of ammonium sulfhydrate in a methanol medium gives a mixture containing 92% of benzyl mercaptan and 8% of benzyl sulphide.

Previous methods do not enable a benzyl mercaptan to be economically obtained meeting the specifications required by users, in particular purity greater than 98% and benzyl chloride content less than 0.1%. Indeed, the separation of benzyl chloride by distillation from crude benzyl mercaptan is very difficult. On the other hand, the formation of byproducts (benzyl sulphide and incidentally benzyl disulphide), although separable by distillation, is prejudicial to the economics of the process. Finally, the use of an alcohol solvent, which has to be recycled or destroyed before being discarded, complicates a production plant.

Thus, there is a need for a process for producing benzyl mercaptan which provides at the same time substantially total conversion of the benzyl chloride and good selectivity for benzyl mercaptan. This is without the use of alcohol as the reaction medium.

SUMMARY OF THE INVENTION

It has now been found that this result can be achieved using ammonium sulfhydrate as long as the operation is carried out under specific conditions, in particular under autogenous pressure in a closed reactor and with a suitable temperature profile.

DETAILED DESCRIPTION OF THE INVENTION

More precisely, the subject of the invention is a process for the preparation of benzyl mercaptan by reacting benzyl chloride and ammonium sulfhydrate in a molar ratio $NH_4SH/C_6H_5CH_2Cl$ of at least 1, preferably between about 1.05 and 1.5. The reaction is carried out under autogenous pressure in a closed reactor in two steps. The first step comprises adding the benzyl chloride to an aqueous solution of ammonium sulfhydrate at a temperature below 80° C. The second comprises heating the reaction mixture to a temperature in the range of 80° to 100° C.

The concentration of the aqueous solution of ammonium sulfhydrate may vary within wide limits because it has no significant effect on the yield or the conversion. However, in practice, it is advantageous to operate with a concentration of $NH_4SH$ of at least 25% by weight to ensure salting-out while hot from the organic phase and consequently a satisfactory decantation. Thus, it is preferable to use an aqueous solution having a concentration of $NH_4SH$ between 25 and 40%.

The equation for the reaction is:

$$NH_4SH + C_6H_5CH_2Cl \rightarrow C_6H_5CH_2-SH + NH_4Cl.$$

It is clear that the molar ratio $NH_4SH/C_6H_5CH_2Cl$ must be at least equal to 1. To promote the complete conversion of the benzyl chloride, it is desirable to use at least a slight excess of ammonium sulfhydrate (for example, about 1.05). A molar ratio $NH_4SH/C_6H_5CH_2Cl$ greater than 1.5 is possible, but does not give any improvement. On the contrary, it needlessly produces a higher pressure due to the decomposition of $NH_4SH$:

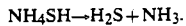
$$NH_4SH \rightarrow H_2S + NH_3.$$

The optimal molar ratio is around 1.2.

In accordance with the process according to the invention, the addition of the benzyl chloride to the aqueous solution of ammonium sulfhydrate must be carried out at a temperature below 80° C., particularly between 0° and 80° C. and preferably at ambient temperature. During the addition, the temperature may be kept at the selected value. It may be increased to reach 80° C. at the end of the addition by exploiting the exothermic nature of the reaction. The duration of the addition of benzyl chloride does not appear to have any effect on the results. It is generally between about 15 minutes and one hour.

Once the addition is complete, the reaction mixture is kept at a temperature in the range 80° to 100° C., preferably at 80°-90° C., until the conversion of the benzyl chloride is substantially complete. The duration of this operation is generally between 1 and 3 hours. The optimal duration is about 2 hours.

After the aqueous phase has been drawn off, the organic phase is advantageously stripped with nitrogen to eliminate the residual hydrogen sulphide. The crude product obtained generally contains more than 95% of benzyl mercaptan and less than 0.1% of residual benzyl chloride. By distillation of this crude product under reduced pressure, a benzyl mercaptan of purity greater than 99% is finally obtained.

EXAMPLES

The following examples illustrate the invention without limiting it.

EXAMPLE 1

Into a 50-liter stainless steel thermostatically controlled reactor, is added 17240 g of 11.8% ammonia solution (which is 120 moles of $NH_3$). Then hydrogen sulphide is added (120 moles) up to the total absorption corresponding to the formation of $NH_4SH$. The temperature of the solution of $NH_4SH$ is kept at about 16° C. The reactor is closed. Addition is made over 30 minutes of 12766 g of benzyl chloride of 99% purity (which is 100 moles). The pressure increases to 3 bars. The temperature is subsequently raised to 80° C. and is kept there for 2 hours. The pressure increases to 7 bars, then falls to 5 bars.

After drawing off the aqueous phase while hot, the organic phase is cooled and a stripping with nitrogen is carried out to eliminate the residual hydrogen sulphide. In this way, 12405 g of a crude product are obtained whose chromatographic analysis shows that it contains 96.7% of benzyl mercaptan, 0.02% of benzyl chloride, 1% of benzyl sulphide and 1.7% of benzyl disulphide. The yield is 96.7% in relation to the benzyl chloride used.

By distillation of this crude product under 2666 Pa, a benzyl mercaptan is obtained having a purity greater than 99%.

EXAMPLE 2

The operation is carried out as in Example 1 except that the addition of benzyl chloride is carried out at 60° C. During the heating to 80° C., the pressure increases to 6 bars, then falls to 4 bars.

The crude product obtained contains 97% of benzyl mercaptan, less than 0.1% of benzyl chloride, 1% of benzyl sulphide and 1.5% of benzyl disulphide.

EXAMPLE 3

Operating as in Example 1, but with only 104 moles of $NH_4SH$, a crude product is obtained containing 96.3% of benzyl mercaptan, less than 0.1% of benzyl chloride, 1.3% of benzyl sulphide and 1.5% of benzyl disulphide.

EXAMPLE 4

Example 1 is repeated under the following conditions:

$NH_4SH$ : 150 moles addition of the benzyl chloride (100 moles) at 20° C. heating at 90° C. for 2 hours.

The pressure increases to 12 bars, then falls to 9 bars. The crude product obtained contains 96% of benzyl mercaptan, less than 0.1% of benzyl chloride, 0.8% of benzyl sulphide and 2.1% of benzyl disulphide.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

I claim:

1. A process for the preparation of benzyl mercaptan, comprising reacting benzyl chloride and ammonium sulfhydrate in a molar ratio $NH_4SH/C_6H_5CH_2Cl$ of at least 1, characterized in that the reaction is carried out in the absence of any organic solvent under autogenous pressure in a closed reactor in two steps, the first comprising adding the benzyl chloride to an aqueous solution of ammonium sulfhydrate at a temperature below 80° C. and the second comprising heating the reaction mixture to a temperature in the range 80° C. to 100° C.

2. The process according to claim 1, wherein the concentration of the aqueous solution of ammonium sulfhydrate is between 25 and 40% by weight.

3. The process according to claim 1, wherein the molar ratio $NH_4SH/C_6H_5CH_2Cl$ is between about 1.05 and 1.5.

4. The process according to claim 3, wherein he molar ratio is about 1.2.

5. The process according to claim 1, wherein during the addition of benzyl chloride, the temperature is permitted to rise to 80° C. at the end of the addition.

* * * * *